US00PP09275P

United States Patent [19]

McGredy

[11] Patent Number: Plant 9,275

[45] Date of Patent: Sep. 5, 1995

[54] FLORIBUNDA ROSE PLANT NAMED 'MACCARLTO'

[75] Inventor: Sam McGredy, Auckland, New Zealand

[73] Assignee: DeVor Nurseries, Inc., Watsonville, Calif.

[21] Appl. No.: 210,325

[22] Filed: Mar. 18, 1994

[51] Int. Cl.[6] ..... A01H 5/00

[52] U.S. Cl. ..... Plt./26

[58] Field of Search ..... Plt. 22, 26, 27

*Primary Examiner*—Howard J. Locker

*Attorney, Agent, or Firm*—Christie, Parker & Hale

[57] ABSTRACT

A new large-flowered floribunda rose plant producing pink blend bicolor flowers.

1 Drawing Sheet

SUMMARY OF THE INVENTION

The present invention relates to a new and distinct variety of rose plant of the floribunda rose class which was originated by crossing as seed parent the variety known as 'Macmiskiz' and as pollen parent the variety known as 'West Coast'. The varietal denomination of this new rose is 'Maccarlto'.

Among the novel characteristics possessed by this new variety which distinguish it from its parents and all other varieties of which I am aware are its attractive pink blend bicolor flowers having classic Hybrid Tea form and size on a truss with widely spaced flowers.

Asexual reproduction by budding of the new variety as performed in Watsonville, Calif. shows that the foregoing and other distinguishing characteristics come true to form and are established and transmitted through succeeding propagations.

COMPARISON WITH PARENTS

'Macmiskiz' produces flowers which are more salmon-colored and much smaller than the new variety. In addition, flowers of 'Maccarlto' have classic hybrid form and 'Macmiskiz' flowers have split centers. The new variety differs from 'West Coast' in that whereas 'West Coast' is a true large Hybrid Tea, 'Maccarlto' is a large-flowered floribunda. The flowers further differ in that the new variety does not have the frilled petals of 'West Coast'.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Macmiskiz'.

*Pollen parent.*—'West Coast'.

Class: Floribunda.

The following is a detailed description of my new variety, of new specimens grown outdoors in New Plymouth, New Zealand in the month of January. The color terminology used is in accordance with the Royal Horticultural Society Colour Chart (RHSCC), and refers to plate numbers in the aforementioned color chart. Phenotypic expression may vary depending on light, environmental and cultural conditions.

FLOWER

Blooming habit: Recurrent.

A. Bud:

(1) *Size.*—Small, about 2 cm to about 2.5 cm long.

(2) *Form.*—Pointed bud.

(3) *Color.*—When sepals first divide, outside near 47B, inside near 39A.

(4) *Sepals.*—Spreading with some pointed leaf ends, upright and longer than bud.

(5) *Peduncle.*—Length: About 12 cm. Aspect: Straight, extremely fine prickles. Strength: Erect, sturdy. Color: Near 146C.

(6) *Bracts.*—None observed.

B. Bloom:

(1) *Size.*—Average size when fully expanded — about 9 cm.

(2) *Borne.*—Several together in sprays of 6–12 blooms.

(3) *Form.*—Imbricated, high-centered at first, becoming flat, petals reflex back quickly.

(4) *Petalage.*—Number of petals under normal conditions — about 55–60.

(5) *Color.*—$\frac{1}{3}$ *to* $\frac{1}{2}$ *open: top surface of outer petals is near* 49A; undersurface of outer petals is near 52D; top surface of inner petals is near 48C; undersurface of inner petals is near 52D; color at base of petals (point of attachment) is near 7D and the general tonality from a distance is straight pink (near 49A). Fully open blooms: top surface of outer petals is near 49B; undersurface of outer petals is near 52D; top surface of inner petals is near 49A; undersurface of inner petals is near 52D; color at base of petals (point of attachment) is near 6D and the general tonality from a distance is straight pink (near 49B). Color of bloom upon aging marginally lightens to a general tonality at a distance near 49D on petal surface and near 49A at the petal edges.

C. Petals:

(1) *Texture.*—Thick, firm.

(2) *Appearance.*—Inside and outside satiny.

(3) *Form.*—Teardrop.

(4) *Arrangement.*—Regularly arranged, imbricated.

(5) *Petaloids.*—Many.

(6) *Fragrance.*—Slight sweet.

(7) *Lasting quality.*—Long-lasting on plant, about 10–14 days and about 8–10 days as cut flower.
(8) *Persistence.*—Drop off cleanly.

REPRODUCTIVE ORGANS

A. Stamens:
(1) *Arrangement.*—Regularly arranged.
(2) *Anthers.*—Color near 21C.
(3) *Filaments.*—Near 21C.
(4) *Pollen.*—Color near 21D.

B. Pistils
(1) *Styles.*—Uneven length.
(2) *Stigmas.*—Color near 7D.

C. Characteristics of hips: Urn-shaped, about 2 cm, orange-scarlet, seeds do not protrude.

PLANT

A. Form: Upright, busky.
B. Growth: Vigorous, about 103 cm at first season.
C. Foliage: Compound 3 and 5 leaflets.
(1) *Size.*—Medium.
(2) *Quantity.*—Abundant.
(3) *Color.*—New foliage — upper side near 146A, underside near 146C; old foliage — upper side near 147A, underside near 148B.
(4) *Shape.*—Elliptic.
(5) *Texture.*—Shiny, smooth, underside matte.
(6) *Edge.*—Serrate.

(7) *Serration.*—Denticulate.
(8) *Leaf stem.*—Color — medium green.
(9) *Stipules.*—Medium length.
(10) *Rachis.*—Small, hooked prickles.
(11) *Petioles.*—Top near 152D, underside near 152D.
(12) *Auricle.*—Long.
(13) *Resistance to disease.*—Blackspot — good; mildew — extra good; rust — good.

D. Wood:
(1) *New wood.*—Near 147B, smooth.
(2) *Old wood.*—Near 146A, smooth.

E. Flower stem: About 70 cm from last cut.

F. Thorns:
*Quantity.*—On main stalk, ordinary; on laterals from stalk, many.
*Form.*—Large, slightly hooked.
*Length.*—Short.
*Color.*—Near 178A when young.
*Position.*—Regular.
*Prickles.*—Very few.

F. Winter hardiness: Wintered well in New Plymouth, New Zealand and in Watsonville, Calif.

I claim:

1. A new and distinct variety of rose plant of the floribunda rose class, substantially as shown and described.

* * * * *

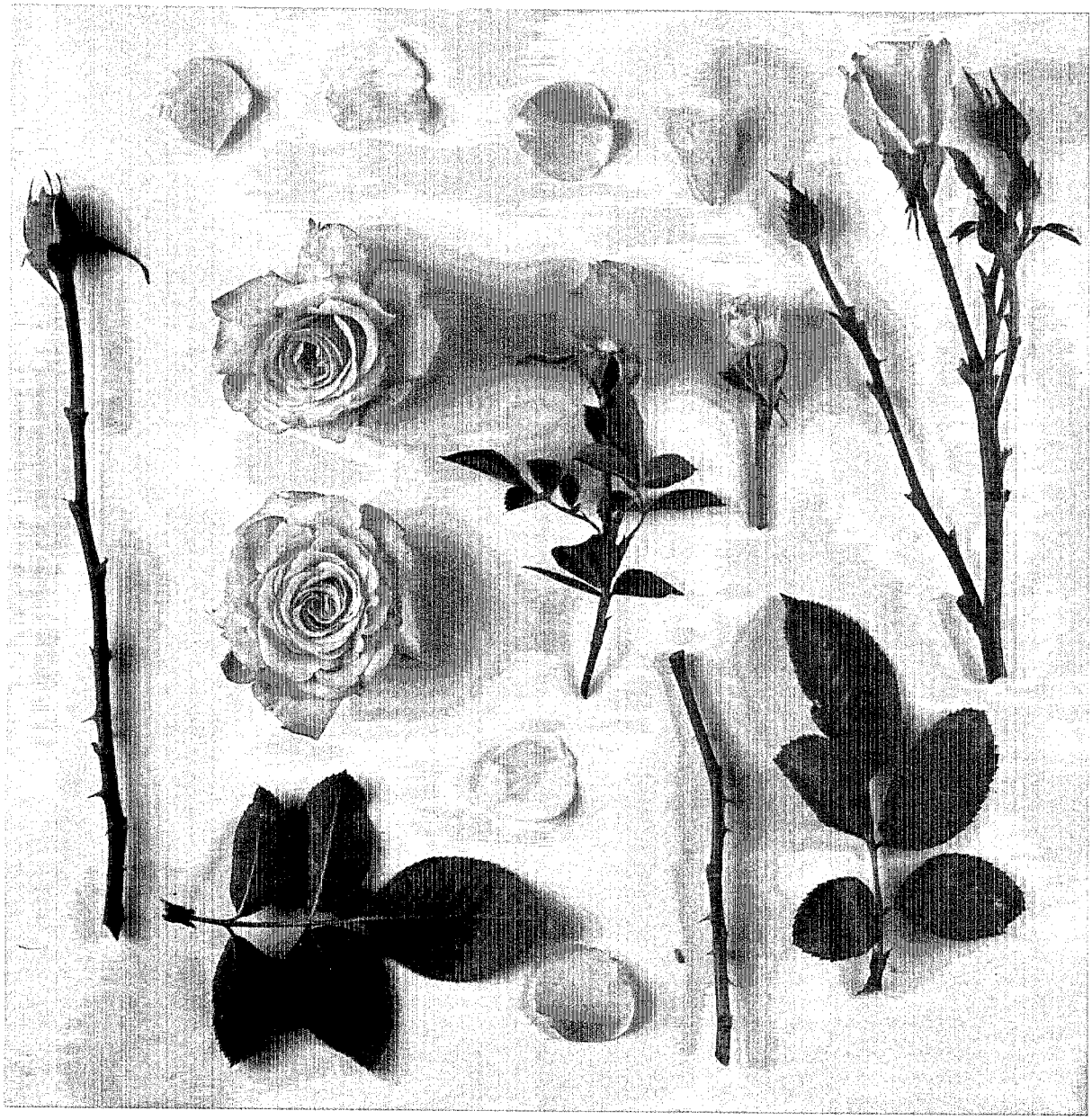

UNITED STATES PATENT AND TRADEMARK OFFICE

CERTIFICATE OF CORRECTION

PATENT NO. : Plant 9,275

DATED : September 5, 1995

INVENTOR(S) : Sam McGredy

It is certified that error appears in the above-indentified patent and that said Letters Patent is hereby corrected as shown below:

Column 3, line 19, change "busky" to -- bushy --.

Signed and Sealed this

Thirteenth Day of February, 1996

*Attest:*

*Attesting Officer*

BRUCE LEHMAN

*Commissioner of Patents and Trademarks*